US00PP30925P2

(12) United States Plant Patent
Elliott et al.

(10) Patent No.: US PP30,925 P2
(45) Date of Patent: Oct. 8, 2019

(54) APPLE TREE NAMED 'CHERRY PARFAIT #19'

(50) Latin Name: *Malus domestica*
Varietal Denomination: Cherry Parfait #19

(71) Applicant: Stark Bro's Nurseries & Orchards Co., Louisiana, MO (US)

(72) Inventors: Lee Elliott, Winchester, IL (US); Mary Elliott, Winchester, IL (US)

(73) Assignee: STARK BRO'S NURSERIES & ORCHARDS CO., Louisiana, MO (US)

( * ) Notice: Subject to any disclaimer, the term of this patent is extended or adjusted under 35 U.S.C. 154(b) by 0 days.

(21) Appl. No.: 15/932,498

(22) Filed: Mar. 7, 2018

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

*Primary Examiner* — Keith O. Robinson
(74) *Attorney, Agent, or Firm* — Sandberg Phoenix & von Gontard PC

(57) ABSTRACT

'Cherry Parfait #19' is a new variety most notably characterized by its fruit. It has the combination of a pink color and a distinct citrus flavor having highlights of lemon, grapefruit, orange and mango. The fruit is firm and crisp, but easily broken apart between the cell walls of the fruit. The 'Cherry Parfait #19' is a ramified type of tree with a spreading tree habit.

11 Drawing Sheets

Latin name: *Malus domestica.*
Varietal denomination: 'Cherry Parfait #19'.

BACKGROUND OF THE INVENTION (1) Field of the Invention

'Cherry Parfait #19' is a new and distinct variety of apple tree (*Malus domestica*).

(2) Description of the Related Art

SUMMARY OF THE INVENTION

The new variety was selected from a population of seedlings derived from crossing the apple varieties PINK LADY® ('Cripps Pink' cultivar, U.S. Plant Pat. No. 7880), male parent, and 'Honeycrisp' (U.S. Plant Pat. No. 7197), female parent, in April 1999 on trees in Winchester, Ill. 'Cherry Parfait #19' has been asexually reproduced through succeeding asexual propagation. All trees were grown at this location.

The seedling tree was grown to the $90^{th}$ node in 2000. The apex scion was removed and limb grafted to limbs of existing 10-year-old Red Delicious (unpatented) apple trees on 'EMLA 7' (unpatented) rootstocks. Fruiting occurred in 2003, and was determined to be of excellent quality. 10 new trees on 'Budagovsky 9 (Bud 9)' (unpatented) and 'EMLA 26' (unpatented) were grafted and set out for test in 2004. All started to fruit by 2008 and all were determined to be exactly like the limb graft and seedling.

'Cherry Parfait #19' has a unique citrus flavor with highlights of lemon, grapefruit, orange and mango, which is otherwise unknown and which neither parent possesses. It has a texture and crispness similar to 'Honeycrisp' and a pink color similar to PINK LADY®, which is a unique combination of traits. 'Cherry Parfait #19' also has a resistance to early fruit drop which is similar to 'Gala' (unpatented) and that is superior to that of either PINK LADY® or 'Honeycrisp.' It has a spreading tree habit, which is dissimilar to either of its to parents, as PINK LADY® is generally upright and 'Honeycrisp' is generally open and semi-upright. No other cultivar is known to exist that is similar.

The newly disclosed and distinct variety/cultivar annually produces fruit that is normally ripe for harvesting and shipping on or about September 25 through October 10 under the ecological and climatological conditions prevailing around approximately the area of Winchester, Ill. The fruit is most notable for its use as a fresh-eating/dessert apple that may also be used for cooking and juicing.

BRIEF DESCRIPTION OF THE DRAWINGS

The photographs submitted herewith show the color of our new variety/cultivar shown at age 5 as nearly as reasonably possible to make the same in a color illustration of this character as follows.

BOTANICAL DESCRIPTION OF THE PLANT

Figure 1:
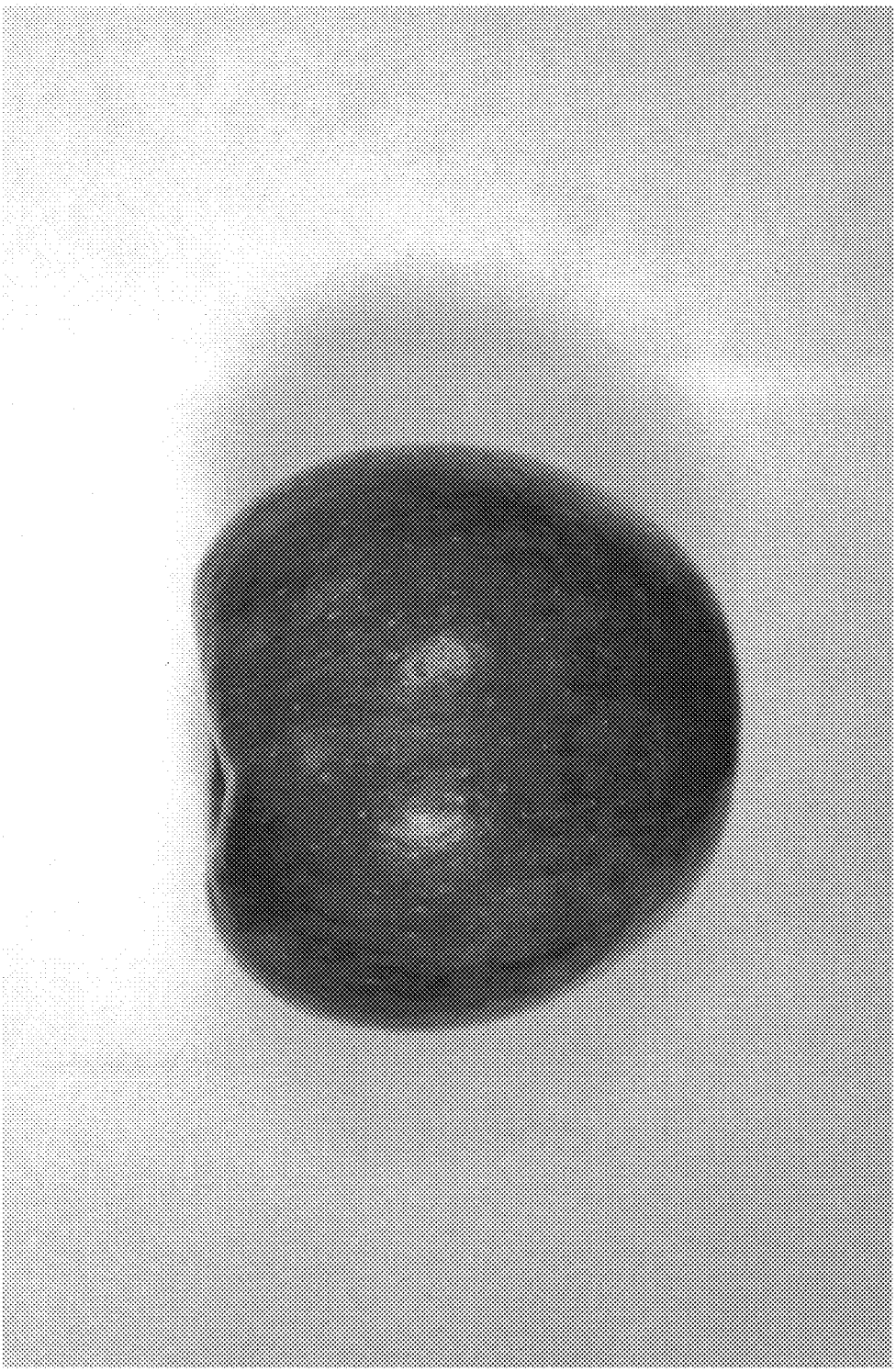
FIG. 1 is a photograph of the fruit of the new and distinct variety apple tree 'Cherry Parfait #19'.
Figure 2:
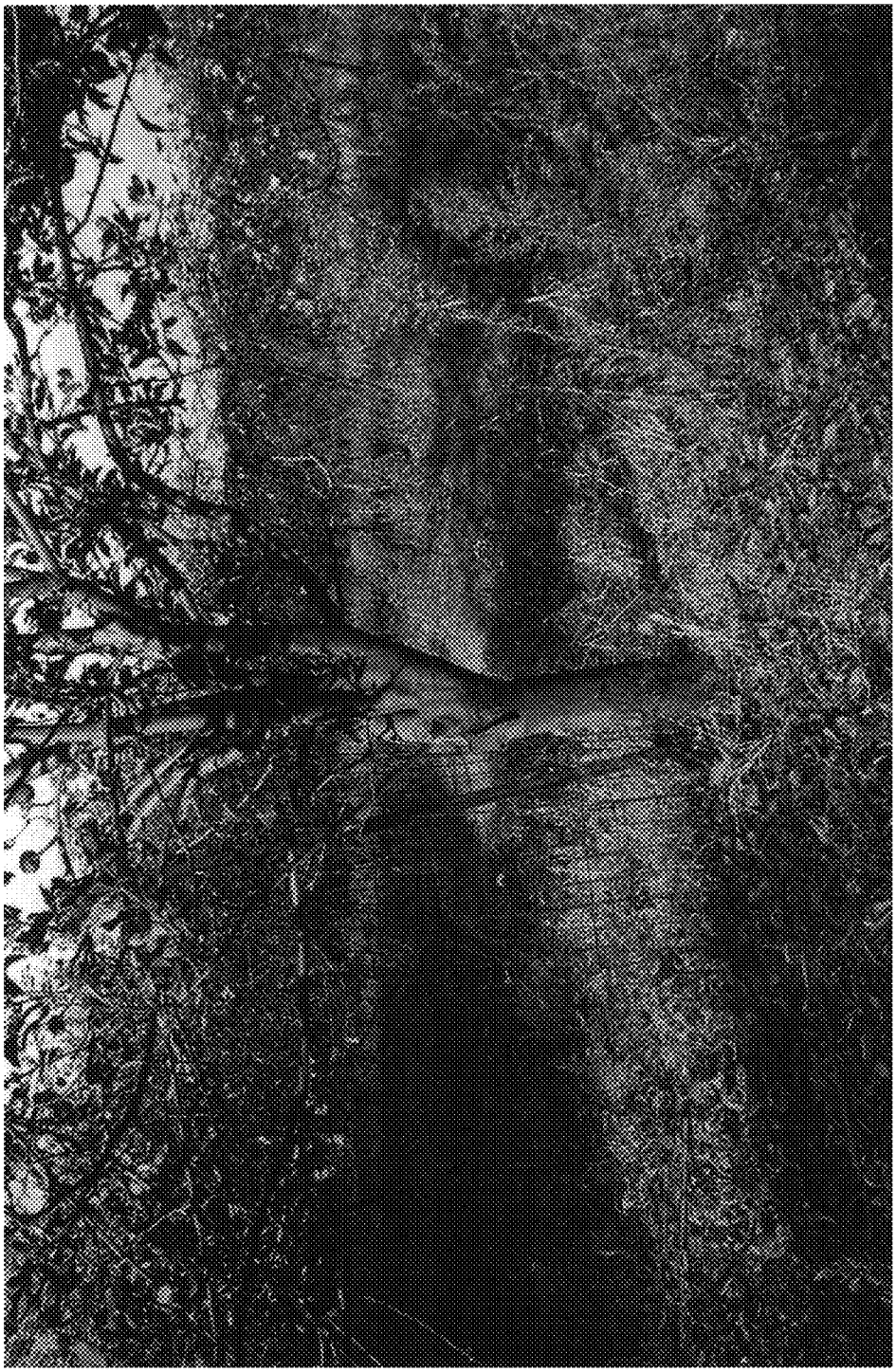
FIG. 2 is a photograph of the trunk and limb habit of the tree.
Figure 3:
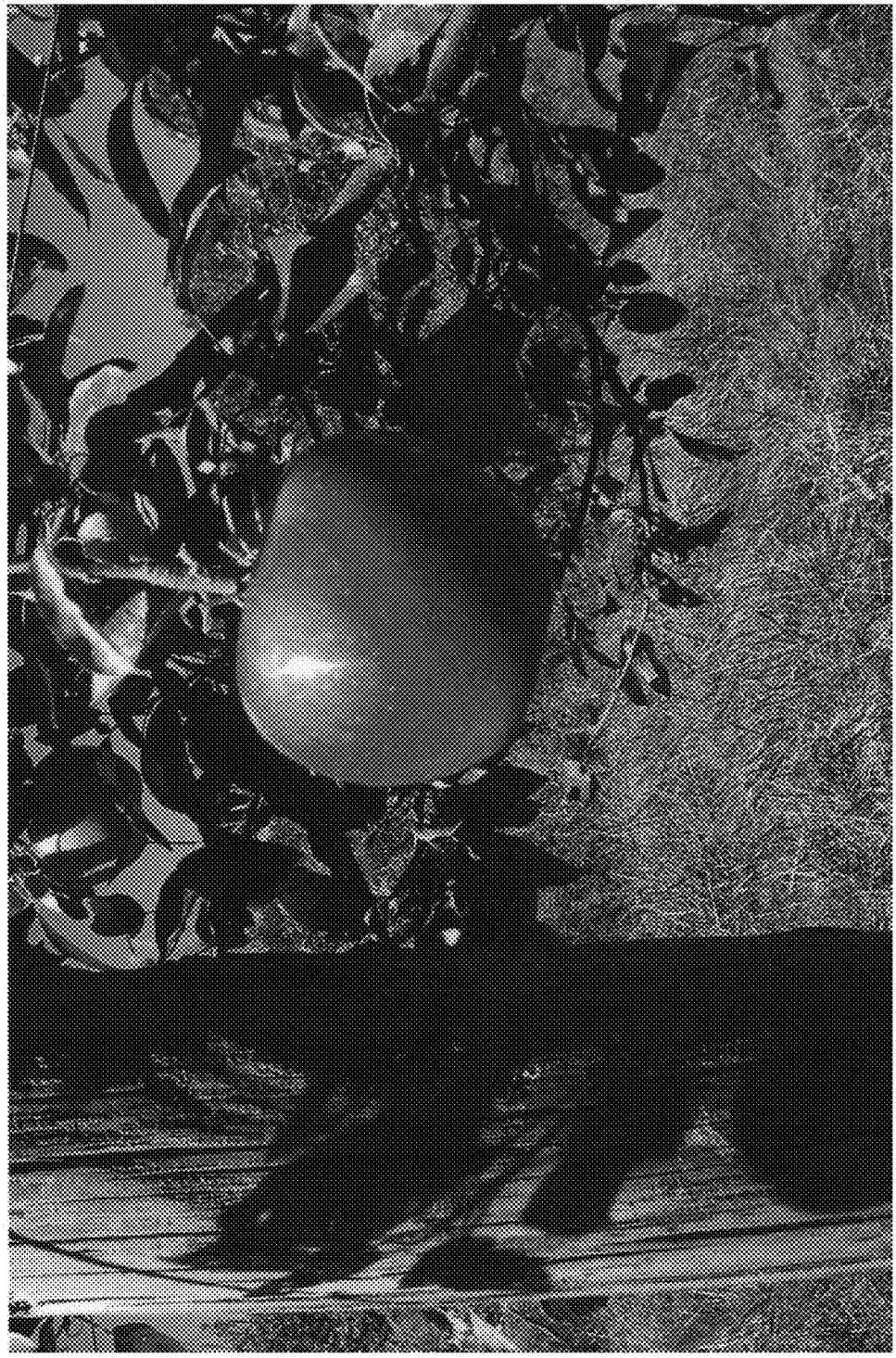
FIG. 3 is a photograph of the fruit and limb habit of the tree.
Figure 4:
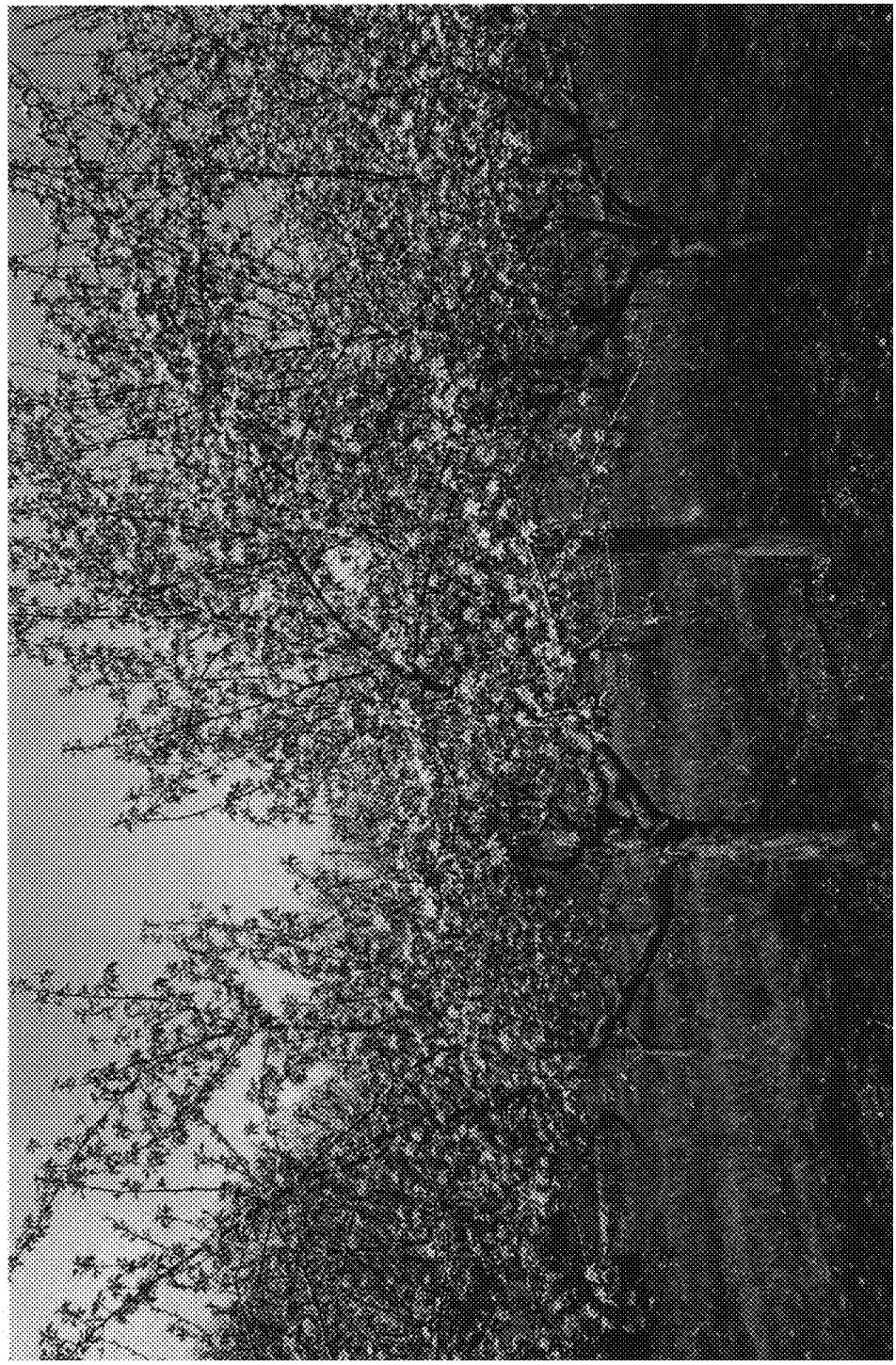
FIG. 4 is a photograph of the blossoms and limb habit of the tree.
Figure 5:
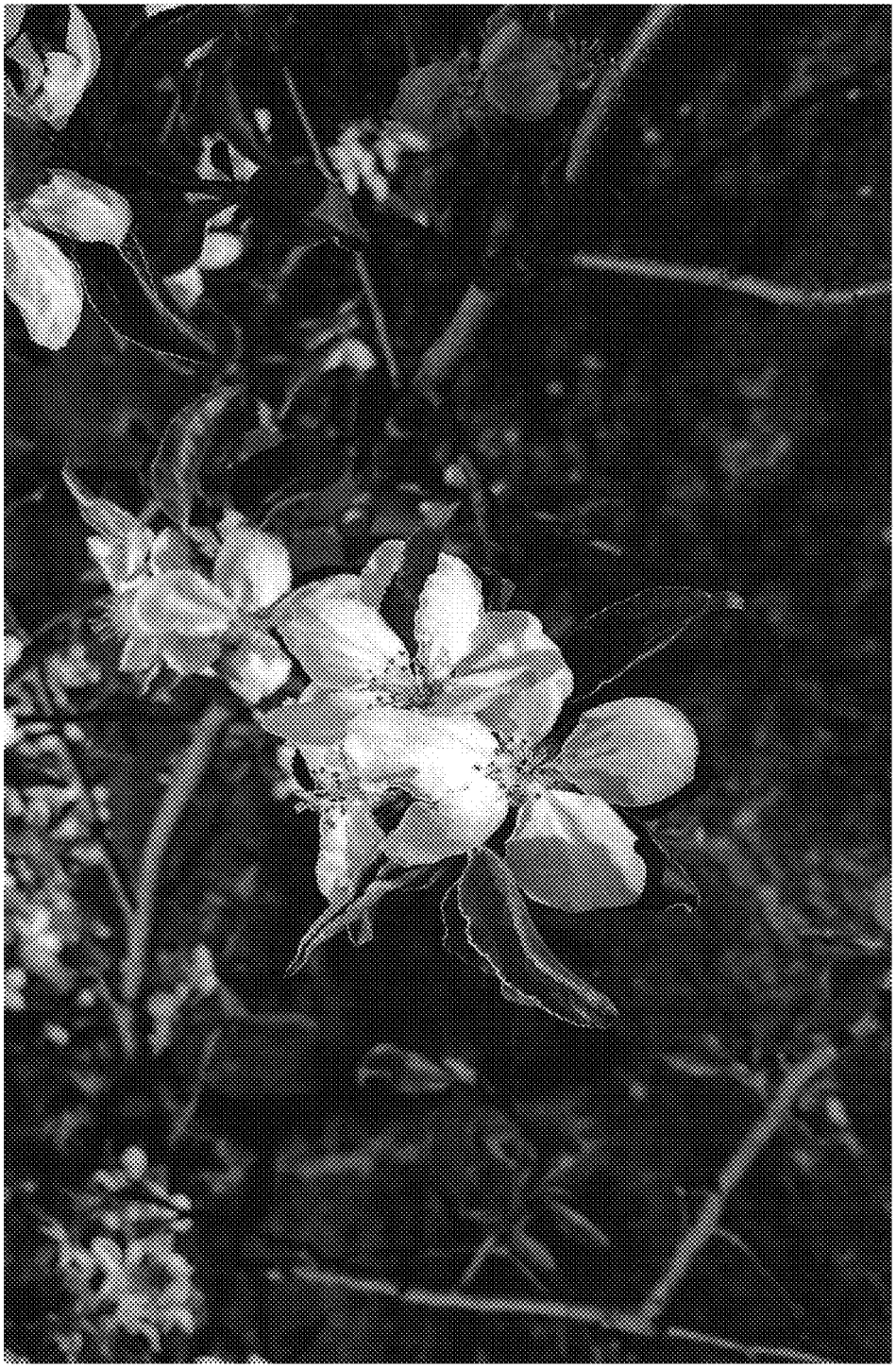
FIG. 5 is a photograph of the open blossoms of the tree.
Figure 6:
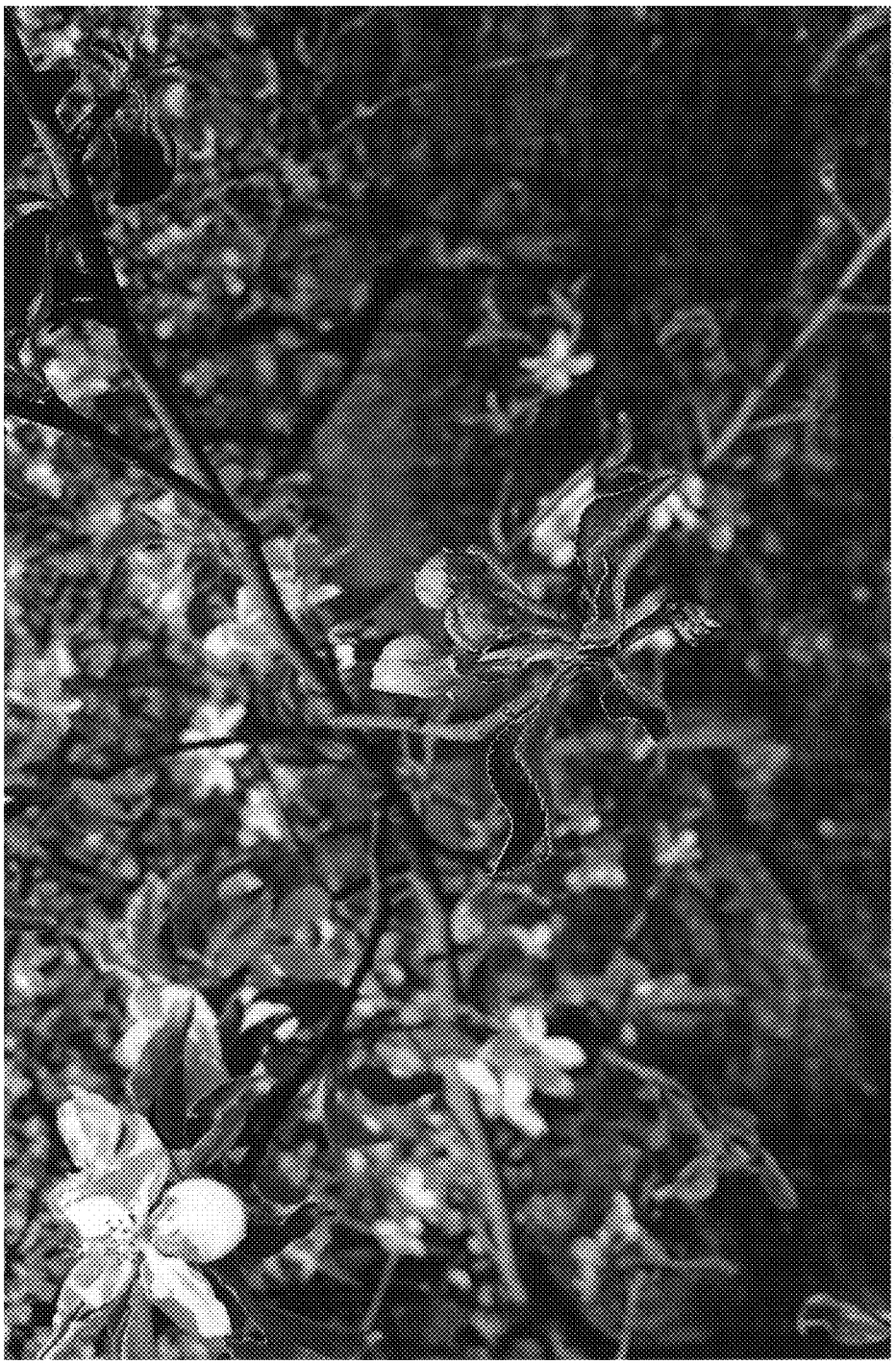
FIG. 6 is a photograph of the closed blossoms of the tree.
Figure 7:
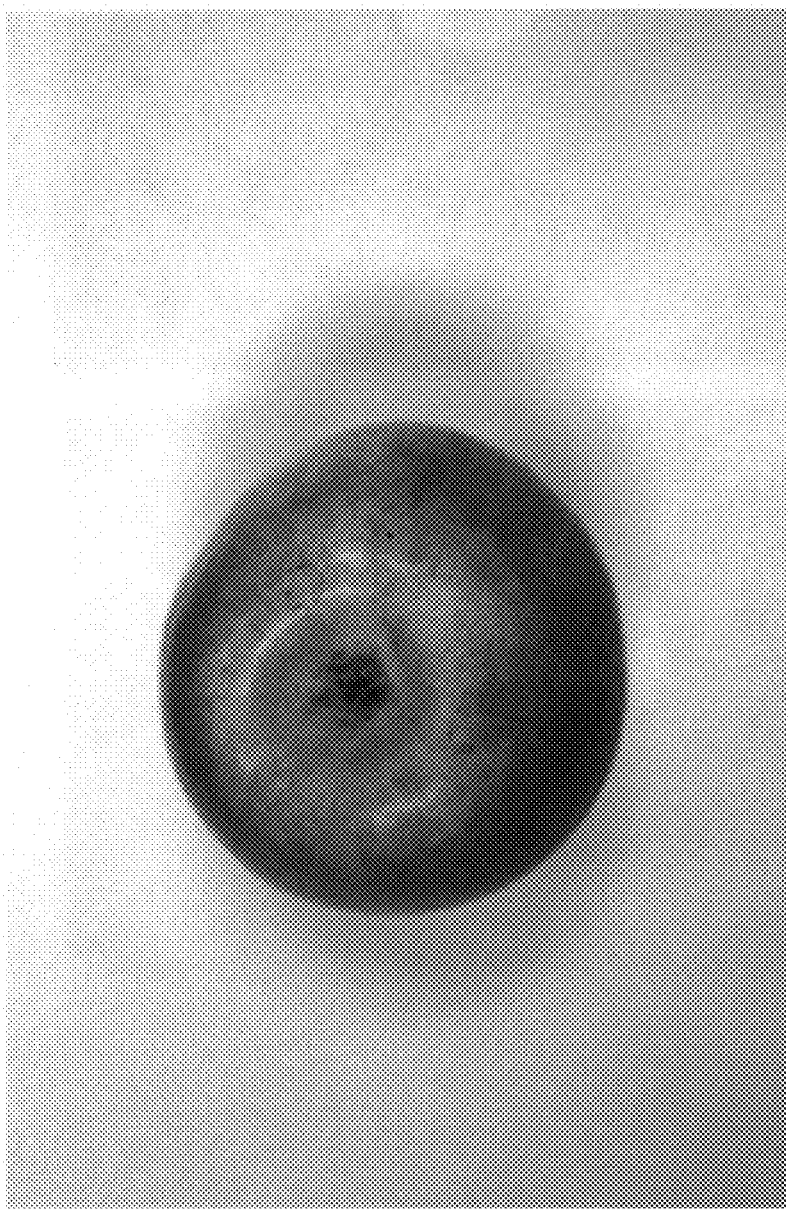
FIG. 7 is a photograph of the 'Cherry Parfait #19' fruit bottom.
Figure 8:
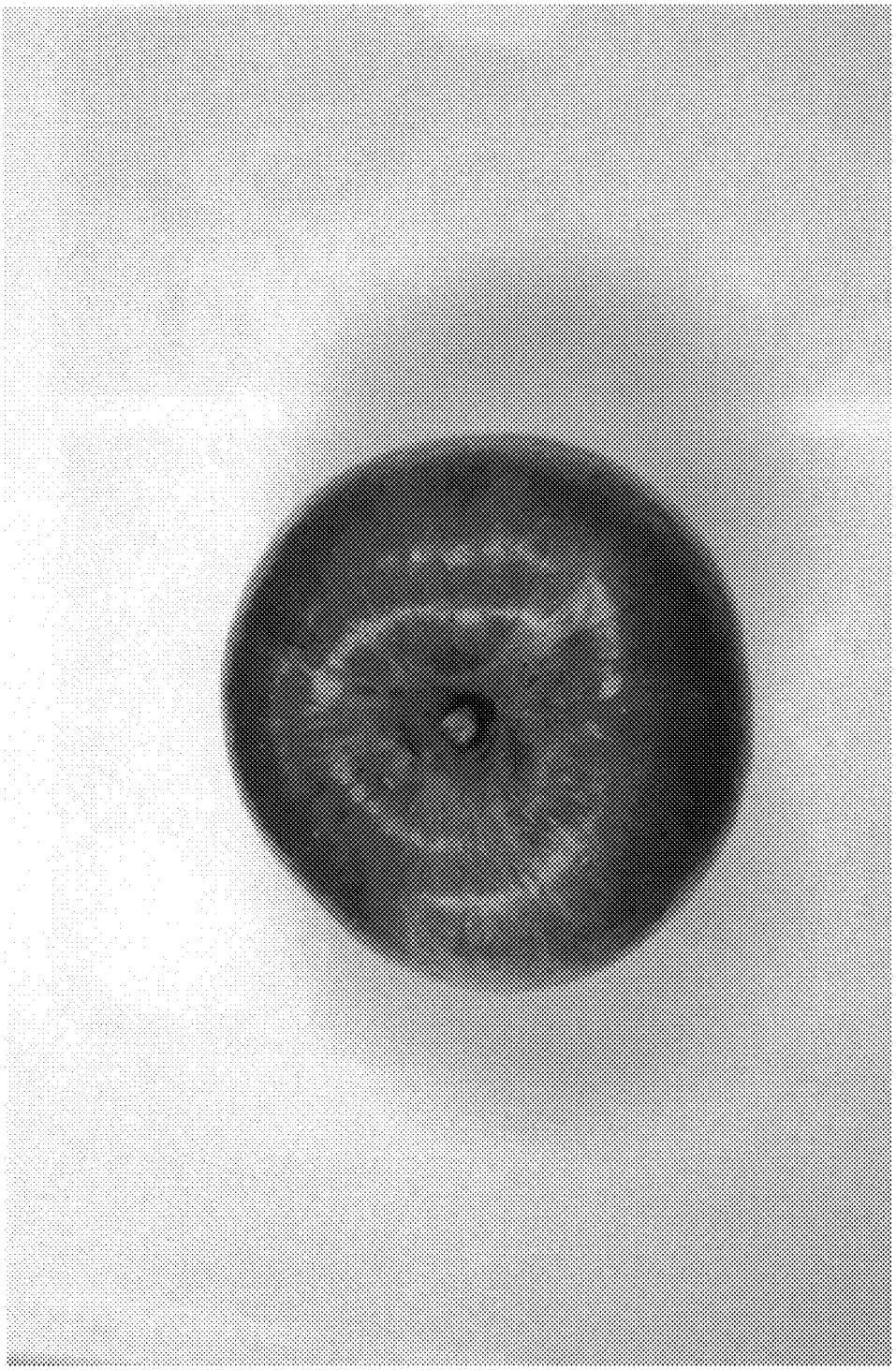
FIG. 8 is a photograph of the 'Cherry Parfait #19' fruit top.
Figure 9:
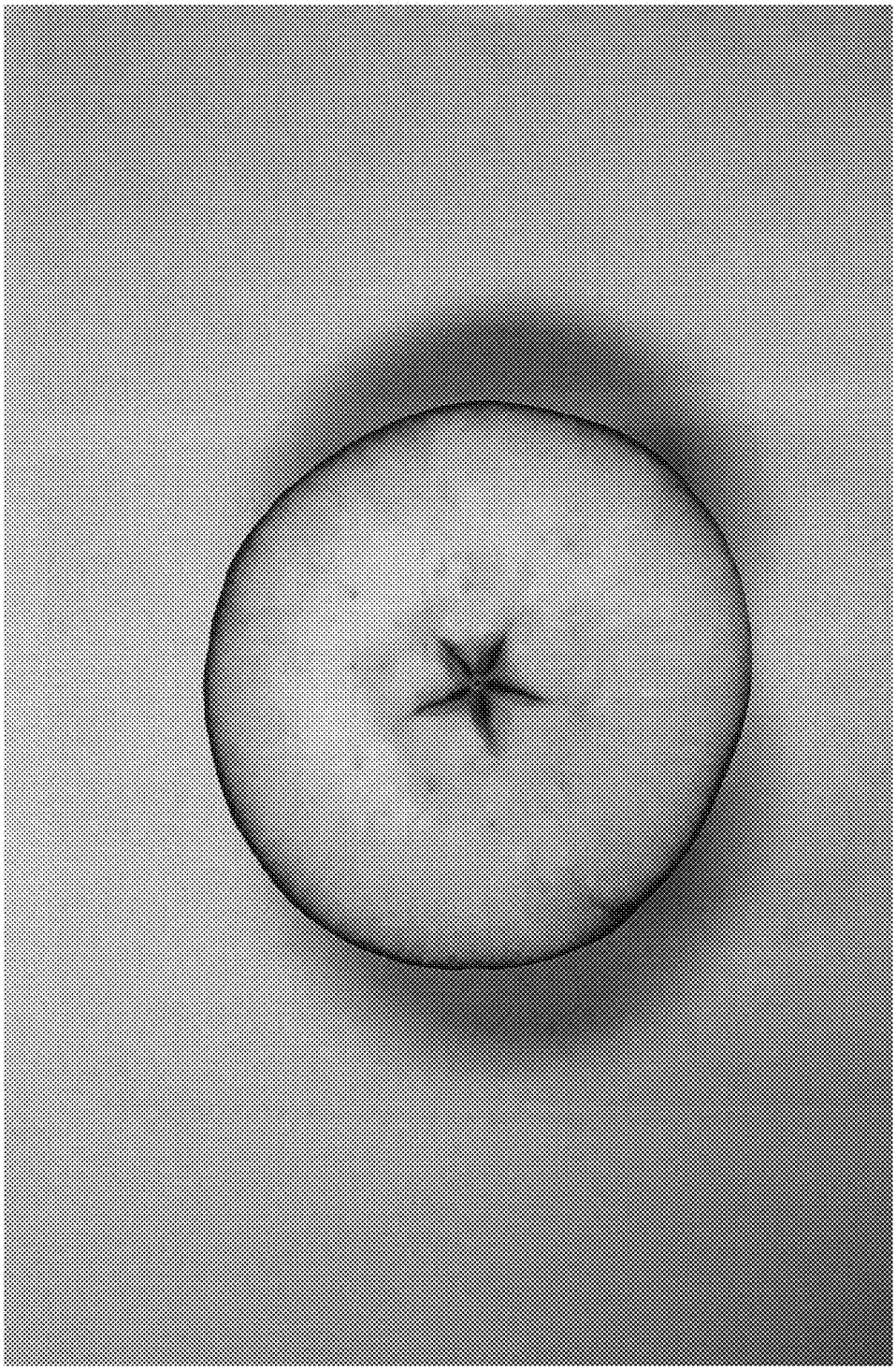
FIG. 9 is a photograph of the 'Cherry Parfait #19' fruit cut in half.
Figure 10:
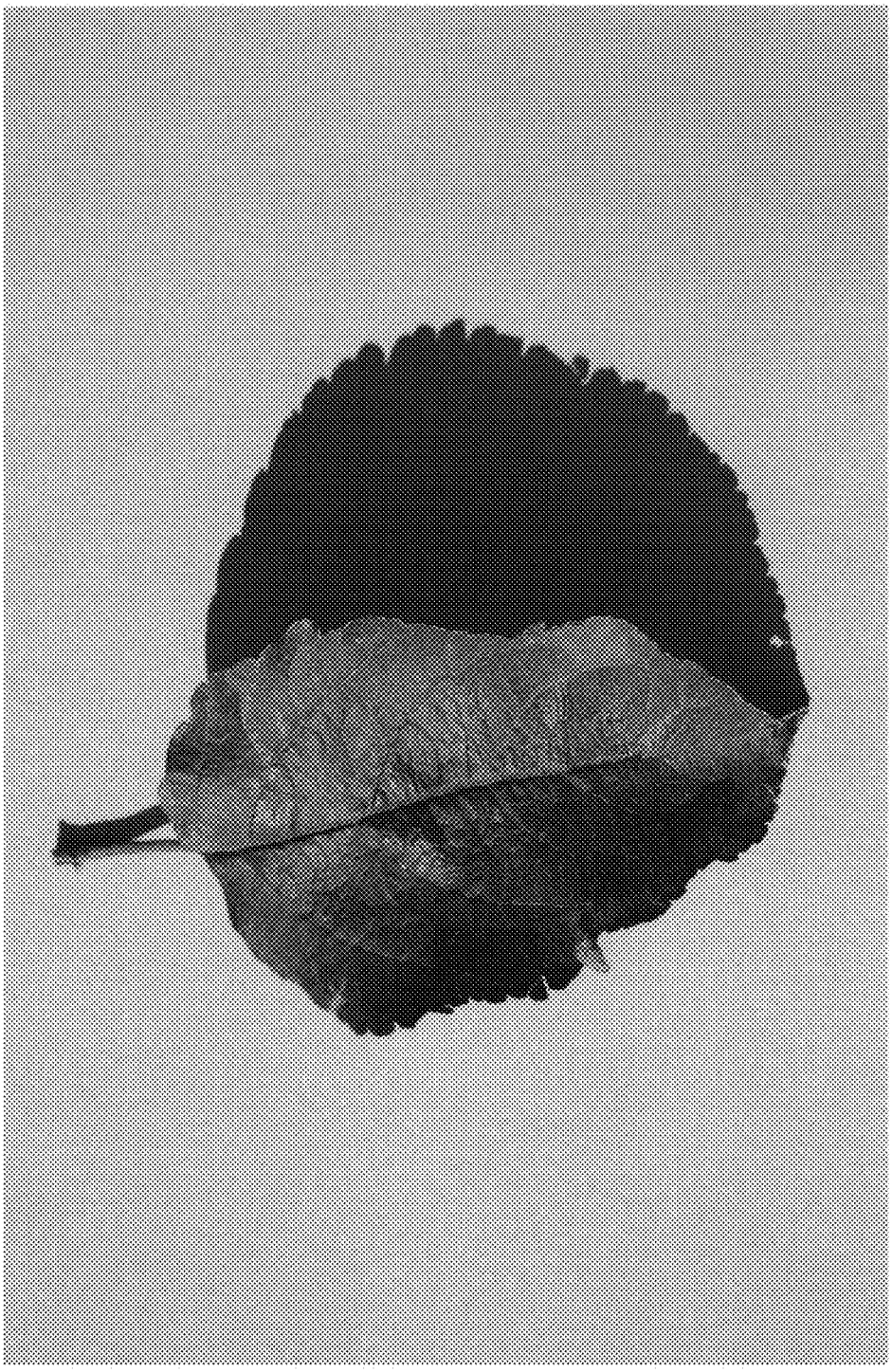
FIG. 10 is a photograph of the tree's leaf top surface.
Figure 11:
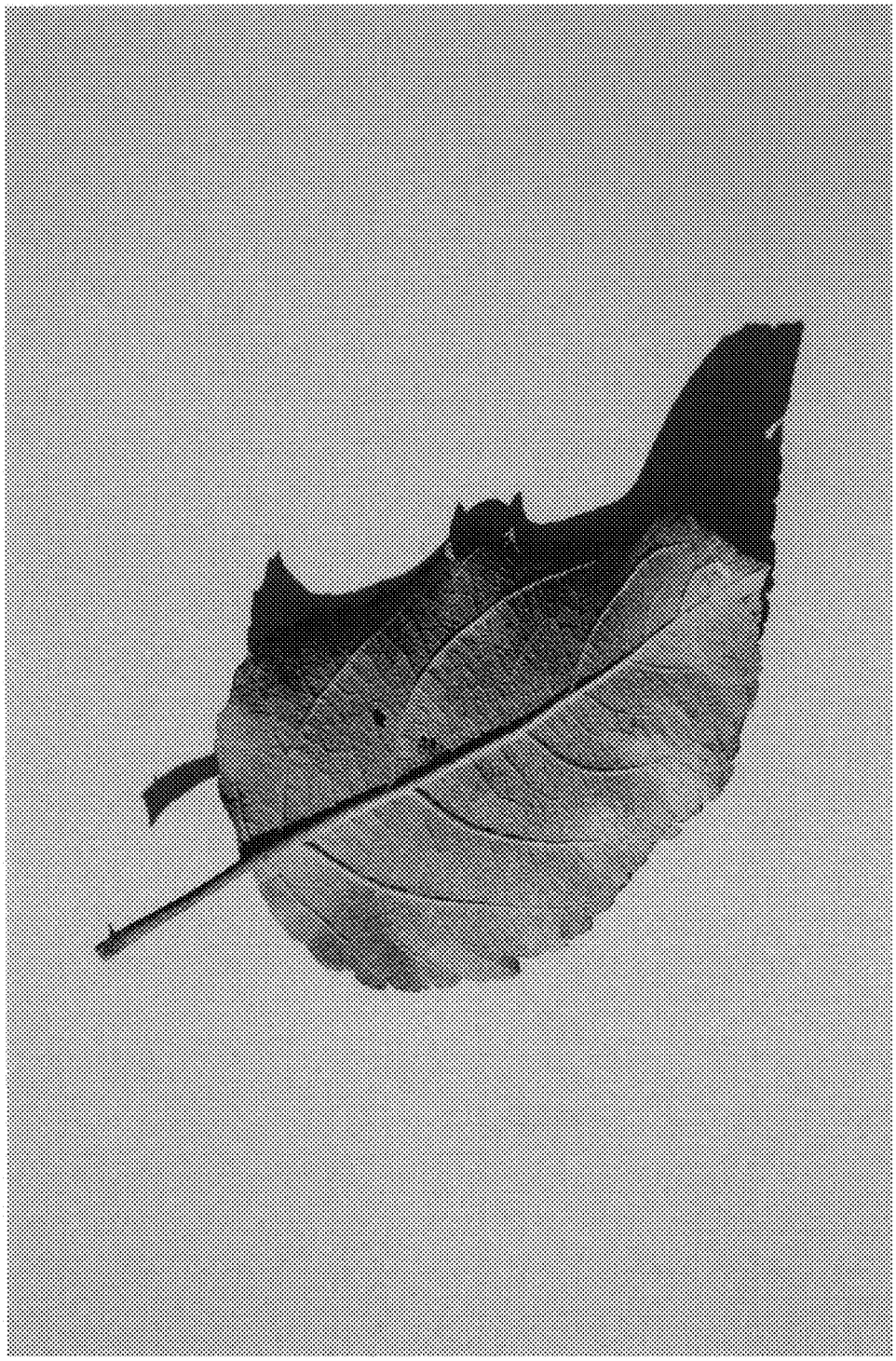
FIG. 11 is a photograph of the tree's leaf bottom surface.

The following is a detailed description of our new cultivar of apple tree, 'Cherry Parfait #19' with color terminology in accordance with The Royal Horticulture Society (R.H.S.) Colour Chart, except where the context indicates a term having its ordinary dictionary meaning. Our new tree has not been observed under all growing conditions and variations may occur as a result of different growing conditions. All progeny of our new variety of 'Cherry Parfait #19' Apple Tree, insofar as have been observed, have been identical in all the characteristics described below.

Parentage: A cross between PINK LADY® ('Cripps Pink' cultivar, U.S. Plant Pat. No. 7780) and 'Honeycrisp' (U.S. Plant Pat. No. 7197) made in April 1999.

Locality where grown and observed: Winchester, Ill.

Tree: 8-year-old tree on M7 rootstock.

- *Size.*—Semi-dwarf.
- *Vigor.*—Medium.
- *Tree type.*—Ramified.
- *Tree form.*—Upright; Spreading.
- *Tree height.*—Approximately 3.8 meters.
- *Tree crown.*—Width. Approximately 4.3 meters.
- *Productivity.*—Very productive. (Yielded 28 Kg in 2015).
- *Regularity of bearing.*—Regular. Bears annually if thinned properly.
- *Trunk diameter.*—11.43 centimeters at 40 centimeter height.

Bark:

- *Surface texture.*—Rough.
- *Bark color.*—Greyed Green (Fan #4, Sheet 198-B).
- *Bark lenticels.*—Numbers — 8 per centimeter area Lenticels — Shape — Elongated Lenticels — Size — 2 millimeter Lenticels — Color — Greyed Orange (Fan #4, Sheet 164-B).

Branches:

- *Size.*—Approximately 6.5 centimeters in diameter.
- *Surface texture.*—Smoother and more glabrous than trunk.
- *Lenticels.*—6 per centimeter area.
- *Upper branches.*—Size — Average 1.7 centimeters diameter.
- *Surface texture.*—Older branches — Smoother than trunk. More glabrous than pubescent new shoots and branches.
- *Older branches.*—Color — Greyed Green (Fan #4, Sheet 197-B).
- *One-year-old shoots and spurs.*—Color — Greyed Green (Fan #4, Sheet 197-B).
- *Current season's shoots.*—Color — Yellow Green (Fan #3, Sheet 144-A).
- *Actively growing shoots.*—Color — Greyed Green (Fan #4, Sheet 197-B).
- *Expanding shoot tips and young leaves.*—Color — Yellow Green (Fan #3, Sheet 144-A).
- *Internode length.*—2.54 centimeters.

Leaves:

- *Leaf length.*—7.3 to 9.0 centimeter range.
- *Leaf width.*—5.0 to 6.0 centimeter range.
- *Leaf thickness.*—Average.
- *Mature leaf texture.*—Top surface is glabrous; Bottom surface is slightly pubescent.
- *Leaf blade attitude in relation to the shoot.*—Upwards.
- *Leaf form.*—Generally — Ovate.
- *Leaf apices.*—Shape — Pointed; Slightly curved.
- *Leaf surface.*—Texture — Pubescent young, immature leaves lose most of their pubescence at maturity.
- *Leaf color.*—Mature leaves — Yellow Green (Fan #3, Sheet 147-B).
- *Color.*—Mid-Vein — (Fan #3, Sheet 147-C).
- *Leaf margins.*—Generally — Serrate; Serrulate; Crenate.
- *Serrations.*—Size — Small.
- *Leaf margins.*—Shape — Undulate.
- *Leaf petiole.*—Size — 2.8 to 4.2 centimeters.
- *Petiole base.*—Shape — Narrow; Very slight flare at base.
- *Petiole.*—Color — Yellow Green (Fan #3, Sheet 147-C).
- *Petiole.*—Surface texture — Lightly pubescent.
- *Immature leaves.*—Surface texture — Medium pubescent.
- *Leaf stipules.*—Generally — 1 millimeter.
- *Leaf stipules.*—Form — Thin and pointed; Tendency to deteriorate from mature leaf petioles.

Flowers:

- *Flower buds.*—Size — Average. 1 centimeter.
- *Flower buds.*—Color — Red (Fan #2, Sheet 63-B).
- *Flower buds.*—Surface texture — Medium pubescence.
- *Bloom time.*—Generally — Mid-to-late April.
- *Date of full bloom.*—Observed at Upstart Nursery on Apr. 18, 2016 and Apr. 28, 2016.
- *Duration of bloom.*—Approximately 10 days.
- *Flower size.*—Generally — 4.5 centimeters wide.
- *Bloom quantity.*—Heavy; Abundant.
- *Flowers per node.*—Five.
- *Petal numbers.*—Five.
- *Petal form.*—Ovate.
- *Petal arrangement on the flower.*—Overlapping.
- *Petal color.*—Pinkish White (Fan #1, Sheet 36-D).
- *Petal claw.*—Shape — Flat narrow.
- *Petal margins.*—Shape — Smooth.
- *Petal apices.*—Form — Rounded.
- *Flower pedicel.*—Size — 2.5 to 3.0 centimeters.
- *Flower pedicel.*—Color — Pale Green (Fan #3, Sheet 145-C).
- *Flower pedicel.*—Surface Texture — Lightly Pubescent.
- *Floral nectaries.*—Color — Yellow Green (Fan #3, Sheet 144-C).
- *Calyx.*—Surface Texture — Medium pubescence.
- *Calyx.*—Color — Light Green (Fan #4, Sheet 144-D).
- *Sepals.*—Surface Texture — Medium pubescence.
- *Sepals.*—Size — 1 centimeter.
- *Sepals.*—Color — Light Green (Fan #3, Sheet 144-D).
- *Anthers.*—Size — 1.5 millimeter.
- *Anthers.*—Color — Pale Yellow (Fan #1, Sheet 11-C).
- *Pollen production.*—Average.
- *Pollen.*—Color — Yellow (Fan #1, Sheet 11-B).
- *Stamens.*—Color — Clear White (Fan #4, Sheet 155-A).
- *Pistil.*—Form — Reniform.
- *Pistil.*—Length — 1 centimeter.
- *Pistil.*—Surface Texture — Smooth; Glabrous.
- *Pistil.*—Color — Yellow Green (Fan #3, Sheet 144-C).

Fruit:

*Maturity when described.*—The fruit of the present variety of the 'Cherry. Parfait #19' apple tree is described at full commercial maturity hereinafter.

*Date of harvest.*—In 2015, the date of harvest was October 1. The date of harvest in 2016 was October 1. The date of harvesting is about October 5. The date of harvesting, noted above, are those that were observed at Winchester, Ill.

*Fruit size.*—Generally — The fruit diameter was about 75 to 85 millimeters adjacent the stem and about 70 to 75 millimeters around the base; the fruit had a height of about 70 to 75 millimeters.

*Size of the eye of the fruit.*—Approximately 12 millimeters.

*Fruit form.*—Generally — Oblong; Regular.

*Fruit symmetry.*—From fully symmetrical to slightly asymmetrical.

*Fruit stem.*—Size — The fruit stem has a length dimension of about 4 to 5 centimeters and a thickness dimension of about 2.5 to 3 millimeters.

*Fruit stem.*—Shape — Straight to slightly curved.

*Fruit stem.*—Color — Yellow Green (Fan #3, Sheet 144-B).

*Fruit stem.*—Surface Texture — Medium pubescence.

*Fruit lenticels.*—Color — Greyed Yellow (Fan #4, Sheet 161-A).

*Stem cavity.*—Shape — Uniform and acute.

*Stem cavity.*—Size — Width is 25 to 30 millimeters. Depth is 13 to 16 millimeters.

*Fruit basin.*—Shape — Symmetrical. Approximately 20 millimeters (breadth) and 13 millimeters (depth).

*Calyx.*—Form — Closed.

*Core.*—Medium. Bundle area — Approximately 22 millimeters in cross-section and 27 millimeters longitudinally Bundle color — Light Green (Fan #3, Sheet 144-D) Core lines — Clasping; in-cross section indistinct Carpellary area — Small; indistinct Calyx tube — Glabrous toward base with a funnel form Stem of funnel — Approximately 19 millimeters Depth of tube to shoulder — Approximately 11 millimeters Entire depth — Approximately 13 millimeters Styles — Present; united toward base; pubescent toward base Stamens — 1 distinct whorl Seed cells — Axile; closed Cell walls — Thin; tough Length — Approximately 45 millimeters Breadth — Approximately 39 millimeters Longitudinal section — Broadly ovate Surface — Smooth Cross-section — Narrow.

*Fruit carpels.*—Generally — 5 present.

*Fruit carpels.*—Shape — Ovate with a point.

*Fruit carpel cells.*—Form — Mostly closed.

*Fruit carpels.*—Surface Texture — Glabrous.

*Seeds.*—Numbers — Approximately 8 to 10.

*Seeds.*—Size — Plump. Length is 6 to 8 millimeters. Width is 3 to 4 millimeters.

*Seeds.*—Thickness — Approximately 2 to 3 millimeters.

*Seed apex.*—Form — Acute.

*Seeds.*—Color — Greyed Purple (Fan #4, Sheet 183-A).

*The color of the seeds at full commercial maturity.*—Greyed Purple (Fan #4, Sheet 187-A).

*Fruit skin.*—Thickness — Average.

*Fruit skin.*—Surface texture — Smooth.

*Fruit skin.*—Flavor — Considered mild to neutral.

*Fruit skin.*—Color — Greyed Red (Fan #4, Sheet 180-B).

*Fruit skin.*—Lenticels — Few to inconspicuous.

*Fruit skin lenticel color.*—Pale Yellow (Fan #1, Sheet 8-D).

*Bloom.*—None.

*Fruit flesh.*—Color — White to Cream Yellow (Fan #1, Sheet 11-D).

*Fruit flesh.*—Texture — Crisp and juicy with large explosive cells.

*Stone cells.*—Generally — Not present; not detected.

*Ripening.*—Generally even. Fruit holds well on the tree. Can be harvested in 2-3 pickings.

*Fruit flavor.*—Sweet, fruity, slight citrus notes.

*Aroma.*—Ambrosial.

*Resistance to insects and diseases.*—Less susceptible to bitter pit (a physiological disorder caused by a calcium deficiency) than parent 'Honeycrisp'; not particularly susceptible to cedar apple rust (gymnosporangium Juniperi-virginianae); some susceptibility to powdery mildew (podosphaera Leucotricha).

*Winter hardiness.*—Hardy: e.g., 6 year old trees survived sustained cold of −10 F. on Jan. 6, 2018.

*Drought/heat tolerance.*—Tolerant; e.g., 6 year old trees survived 8 weeks of steady drought in the summer of 2018.

We claim:

1. A new and distinct apple tree substantially as described and illustrated herein.

* * * * *